United States Patent [19]

Tius

[11] Patent Number: 5,349,112
[45] Date of Patent: Sep. 20, 1994

[54] CYCLIC ANTI-TUMOR PROMOTER COMPOUNDS, COMPOSITIONS AND METHODS FOR PRODUCTION AND USE

[75] Inventor: Marcus A. Tius, Kailua, Hi.

[73] Assignee: University of Hawaii, Honolulu, Hi.

[21] Appl. No.: 157,425

[22] Filed: Nov. 26, 1993

Related U.S. Application Data

[63] Continuation of Ser. No. 854,414, Mar. 19, 1992, Pat. No. 5,276,217.

[51] Int. Cl.$^5$ ............... C07C 35/205; C07C 63/64; C07C 69/76; A01N 31/00
[52] U.S. Cl. ............... 514/532; 514/480; 514/546; 514/738; 514/739; 514/533; 560/104; 560/128; 560/126; 562/495; 562/510; 568/715; 568/722; 568/723; 568/834; 568/821
[58] Field of Search ............... 514/738, 739, 480, 546; 560/104, 128; 562/510, 495; 568/715, 822, 823, 821, 834

[56] References Cited

U.S. PATENT DOCUMENTS

| | | | |
|---|---|---|---|
| 4,181,631 | 1/1980 | Shaffer et al. | 560/231 |
| 4,214,098 | 7/1980 | de Jong et al. | 560/231 |
| 4,631,147 | 12/1986 | Matsumoto et al. | 252/522 R |
| 4,701,570 | 10/1987 | Mizusaki et al. | 568/821 |
| 4,906,794 | 3/1990 | Umezu | 568/821 |
| 4,916,160 | 4/1990 | Morital | 514/546 |
| 5,276,217 | 1/1994 | Tius | 568/821 |

FOREIGN PATENT DOCUMENTS 56-61317 5/1981 Japan.
56-61318 5/1981 Japan.

OTHER PUBLICATIONS

Kobayashi et al. "Chem. Pharm. Bull." 38(3):815-817 (1990).
Fujiki et al. "J. Cancer Res. Clin. Oncol." 115:25-28 (1989).
Troll, "Free Rad. Res. Comms." 12-13 (2):751-757 (1991).
Mato. et al. "Jpn. J. Clin. Oncol." 20 (3):219-224 (1900).
Narisawa et al. "Cancer Res." 49(12):3287-3289 (1989).
McMurry et al. "Tetrahedron Letters" 30(10)1173-1176 (1989).
Takayanagi et al. Tetrahedron Letters 31(23):3317-3320 (1990).
Crowell et al. J. Biol. Chem. 266(26):17679-17685 (1991).

*Primary Examiner*—Werren B. Lone
*Attorney, Agent, or Firm*—Oblon, Spivak, McClelland, Maier & Neustadt

[57] ABSTRACT

Novel cyclic anti-tumor promoter compounds and therapeutic compositions are disclosed, along with method for their production and use as anti-cancer and cancer-prevention agents.

25 Claims, 7 Drawing Sheets

EE = -CHOCH₂CH₃ (with CH₃ branch)

CYCLIC ANTI-TUMOR PROMOTER COMPOUNDS, COMPOSITIONS AND METHODS FOR PRODUCTION AND USE

LICENSE RIGHTS

Certain embodiments of this invention were made with Government support under Grant No. 5R01CA45288, awarded by the National institutes of Health, National Cancer Institute. The Government has certain rights in this invention.

This is a continuation division, of application Ser. No. 07/854,414, filed on Mar. 19, 1992 now Pat. No. 5,276,217.

TECHNICAL FIELD

The present invention relates generally to compounds, therapeutic compositions and methods for preventing and treating cancers, and more specifically to useful synthetic cyclic anti-tumor promoter compounds, therapeutic compositions and methods for their production and use.

BACKGROUND OF THE INVENTION

It is well known that cellular DNA can be modified by a variety of agents, occasionally resulting in the creation of a new cell species, such as tumor cells. The fact that carcinogenic agents appear to be prevalent in the environment, coupled with the relatively low occurrence of cancer in certain populations, has suggested the presence of major anti-carcinogenic factors in the environment as well.

The multi-stage nature of carcinogenesis has been previously shown for skin cancer (Berenblum, I., Cancer Res., 1, 44, 1941). In this pioneering work, inflammatory croton oil, when painted on the backs of mice, caused tumors only when the mice were pretreated with a minute dose of a carcinogen that by itself would be insufficient to cause cancer. It has been postulated that a carcinogen gives rise to a cell type indistinguishable from normal cells until exposure to a promoting agent converts it to a tumor cell. Many known tumor promoters are derivatives of 12-O-tetradecanoylphorbol-13-acetate (TPA), the parent alcohol of the tumor promoting compounds of croton oil. Other types of tumor promoting agents include teleocidin, aplysiatoxin and okadaic acid.

Current hypotheses recognize three phases in tumor development: Stage 1—initiation, Stage 2—promotion, and Stage 3—progression to malignant neoplasm. In contrast to tumor initiation, multiple applications or prolonged exposure to a tumor promoting agent are believed to be required before tumor growth becomes inevitable. The extended nature of Stage 2 appears to provide an opportunity to prevent tumor formation by utilizing dietary and other components which inhibit the effects of tumor promotion agents.

The mechanism of tumor promotion displays a number of common characteristics among the seemingly unrelated agents which contribute to cancer, including protein kinase C activation, protease activity, induction of oxygen radicals and poly(ADP)ribose polymerase. Thus, as might be expected, numerous agents have been shown to have some activity a anti-tumor promotor agents. Such agents include protease inhibitors, retinoids, sarcophytols and nicotinamides. These agents appear to share two characteristic properties: they suppress oxyradical induction of tumor promoter-induced neutrophils and they prevent oncogene transformation in ras-induced NIH 3T3 cells.

Activated (i.e. mutated) ras genes have been found in 10 to 20% of all human cancers. Over 90% of pancreatic cancers, 50% of colorectal cancers and 30% of lung cancers have activated ras genes. A single topical application of 7,12-dimethylbenz[a]anthracene to mouse skin can induce a mutation in codon 61 of c-H-ras gene in the affected cells.

The ras genes encode guanine nucleotide binding proteins that participate in the control of eukaryotic cell proliferation. Ras proteins associate with the inner surface of the plasma membrane through the farnesyl and palmitoyl groups. Ras proteins have two states: A GTP-bound active state and a GDP-bound inactive state. Active ras protein is converted to an inactive form by an intrinsic guanosine triphosphatase (GTPase) activity that is stimulated by interaction with a GTPase activating protein (GAP). Upon binding GTP, ras proteins become activated and are capable of stimulating cell proliferation. Mutated ras proteins decrease their intrinsic GTPase activity by a conformational change in the guanine nucleotide binding site of the protein or by a nonproductive association with GAP protein. Therefore, the mutated ras protein remains in the active conformation longer (Schafer, W. R. et al., Nature, 28, 379 (1989)).

However, compounds presently known to be useful as anti-tumor promoters typically have one or more drawbacks, including low activity, high cost of manufacture and toxicity. Thus it is considered desireable to develop a highly active antitumor promoter compound which is relatively nontoxic and inexpensive to manufacture.

DESCRIPTION OF THE PRIOR ART

Compounds sharing certain structural attributes with those of the present invention have previously been described. For example, the cembrane-type diterpenes Sarcophytol A & B, isolated from the soft coral Sarcophyton glaucum, have been shown to have anti-tumor promoter activity (U.S. Pat. Nos. 4,906,794 and 4,916,160).

In addition, 1-methyl-4-(methylethenyl) cylcohexene (Limonene), a component of various ethereal oils such as oils of lemon, orange, caraway, dill and bergamot, although structurally somewhat similar to compounds of the present invention, has not been shown to have substantial anti-tumor promoter activity (Russin, W. A. et al., Carcinogenesis, 10:2161 (1989), Maltzman, T. H. et al., Carcinogenesis, 10:781 (1989)).

Also, (S)-5-Hydroxy-1-(4-hydroxy-3-methoxyphenyl)-3-decanone (Gingerol), the major phenol component of ginger oil, shares certain structural features with compounds of the present invention. Gingerol has been reported to be an inhibitor of tumor promotion (Muto, Y. et. al., Jpn. J. Clin. Oncol., 20:219, p. 221 FIG. 1 (1990)) although the text of the reference (p. 222) does not directly support this assertion.

DISCLOSURE OF THE INVENTION

The present invention provides synthetic cyclic anti-tumor promoter compounds, therapeutic compositions containing such compounds, and methods for their production and use as anti-tumor promoter agents for preventing and treating cancers.

In the practice of the instant invention, there is provided at least one cyclic anti-tumor promoter compound in accordance with the formula:

(I)

wherein:
the bond between $C_2$ and $C_3$ can be a single or a double bond;
X is an alkylene or alkenylene group with a $C_{1-9}$ backbone;
$R_1$ is $OR_5$, wherein $R_5$ is H, an alkyl or acyl group having 1 to 6 carbon atoms, or $CO_2R_6$, wherein $R_6$ is H or an alkyl group having 1 to 6 carbon atoms;
$R_2$ is H, or an alkyl or alkenyl group having 1 to 6 carbon atoms;
each of $R_3$ and $R_4$ is independently H, an alkyl or alkenyl group having 1 to 6 carbon atoms, or a phenyl group which may be attached via an alkyl or alkenyl group having 1 to 6 carbon atoms, or a halogen atom, or $R_3$ and $R_4$ make be taken together to form a methylidene, an alkylidene having 1 to 6 carbon atoms, or an arylidene group; and
Y is H, OH or an O-acyl substituent group; with the proviso that:
when X is when specified in the $C_4$ to $C_n$ direction, then the bond between $C_2$ and $C_3$ is a single bond.

Typically, representative anti-tumor promoter compounds employed in the practice of the invention comprise a central $C_{6-14}$ cyclic moiety, an optional double bond between the $C_2$ and $C_3$ carbons, at least one alkyl substituent group at the $C_4$ carbon, and a hydroxyl or O-alkyl substituent group at the $C_1$ carbon.

Also provided in accordance with aspects of the invention are pharmaceutical compositions useful as anti-cancer and cancer-prevention agents, which compositions contain the above-recited anti-tumor promoter compounds together with a pharmaceutically acceptable carrier. Administration of therapeutically effective doses of these compositions can provide effective delivery of the above-recited biological activities to mammalian hosts.

Additional aspects of the present invention provide methods for producing such useful compounds and compositions, and methods for using the compounds and compositions as therapeutic agents.

DETAILED DESCRIPTION OF THE INVENTION

The present invention provides cyclic anti-tumor promoter compounds, therapeutic compositions containing such compounds, and methods for their production and use as anti-tumor promoter agents for preventing and treating cancers.

It is known that sarcophytol A, a marine natural product derived from a soft coral displays antitumor promoting properties. However, the problems associated with its availability from the natural source and the expense of synthesizing it in large quantities, suggest that a simpler analog which preserves its activities would be desirable.

Surprisingly, it has been determined that conformationally restricted analogs of sarcophytol A which retain certain essential features of the natural product will provide compounds with improved anti-tumor promoter activities.

Thus, in accordance with one aspect of the subject invention, there is provided at least one cyclic anti-tumor tumor promoter having the general structure of a compound in accordance with the formula:

(I)

Wherein:
the bond between $C_2$ and $C_3$ can be a single or a double bond;
X is an alkylene or alkenylene group with a $C_{1-9}$ backbone;
$R_1$ is $OR_5$, wherein $R_5$ is H, an alkyl or acyl group having 1 to 6 carbon atoms, or $CO_2R_6$, wherein $R_6$ is H or an alkyl group having 1 to 6 carbon atoms;
$R_2$ is H, or an alkyl or alkenyl group having 1 to 6 carbon atoms;
each of $R_3$ and $R_4$ is independently H, an alkyl or alkenyl group having 1 to 6 carbon atoms, or a phenyl group which may be attached via an alkyl or alkenyl group having 1 to 6 carbon atoms, or a halogen atom, or $R_3$ and $R_4$ make be taken together to form a methylidene, an alkylidene having 1 to 6 carbon atoms, or an arylidene group; and
Y is H, OH or an O-acyl substituent group; with the proviso that:
when X is when specified in the $C_4$ to $C_n$ direction, then the bond between $C_2$ and $C_3$ is a single bond.

One class of representative cyclic anti-tumor promoter compounds employed in the practice of the invention comprises compounds wherein X is a $C_1$ (methylene) linking group.

Such compounds are generally in accordance with the formula:

(II)

Wherein the $C_2$–$C_3$ bond, R groups and Y are as previously defined.

Included within the class of compounds disclosed in formula II are compounds wherein the R groups are H or $C_{1-3}$ saturated or unsaturated substituent groups, such as methyl ($CH_3$), ethyl ($CH_2CH_3$), ethenyl (=$CHCH_3$), propanyl ($CH_2CH_2CH_3$), propenyl (CH=$CHCH_3$), isopropanyl ($CH(CH_3)_2$), isopropenyl (C(=$CH_2$)$CH_3$), isopropylidiene (=C($CH_3$)$_2$) and methylethenyl ($CH_2CH$=$CH_2$) groups, among others. Such compounds are generally in accordance with the formula:

(III)

Wherein:
the $C_2$–$C_3$ bond is a double bond, the R groups are each independently H or $C_{1-3}$ saturated or unsaturated substituent groups as previously defined,
with the proviso that:
when $R_2$ is H, then $R_3$ and $R_4$ are not taken together to represent methylidene or ethylidene.

Selected cyclic anti-tumor promoter compounds utilized in the practice of the present invention include those compounds of formula III as disclosed above. Such compounds are deemed desirable for their potent anti-tumor promoter activity coupled with their low cost and relative ease of synthesis.

Representative cyclic anti-tumor promoter compounds of the invention as disclosed in formula III include:

A second class of cyclic anti-tumor promoter compounds employed in the practice of the invention comprises compounds wherein X is a $C_{2-9}$ backbone linking group. Such compounds are generally in accordance with the formula:

(IV)

Wherein:
X is an alkylene or alkenylene group with a $C_{2-9}$ backbone; and
the $C_2$–$C_3$ bond, R groups and Y are as previously defined,
with the proviso that:
when X is when specified in the C₄ to $C_n$ direction, then the bond between $C_2$ and $C_3$ is a single bond.

Included within the class of compounds disclosed in formula IV are compounds wherein the R groups are H or $C_{1-3}$ saturated or unsaturated substituent groups, such as methyl, ethyl, ethenyl, propanyl, propenyl, isopropanyl, isopropenyl, isopropylidiene and methylethenyl groups, among others.

Representative cyclic anti-tumor promoter compounds of the invention as disclosed in formula IV include:

Although the usefulness of the present invention is not dependent upon the validity of any particular theory, it is believed that the present compounds and compositions operate to inhibit the farnesylation of ras-p21 in the following manner.

Isoprenylation appears to be essential for the association of oncogenic ras proteins with the cell membrane, as evidenced by the loss of transforming ability when isoprenylation is blocked. Isoprenylation is accomplished by farnesylation in the ras protein (Maltese, W. A., The FASEB Journal, 4, 3219 (1990)). Farnesylpyrophosphate transferase consists of two subunits: A catalytic subunit of 46kDa and a regulatory subunit of 49kDa. Ras protein binds to the regulatory subunit and Farnesylpyrophosphate binds to the catalytic subunit. It is not presently clear how the compounds of the present invention accomplish the inhibition of farnesylation; it is probable that the compounds inhibit the interaction between ras protein and Farnesylpyrophosphate.

Figure 1:
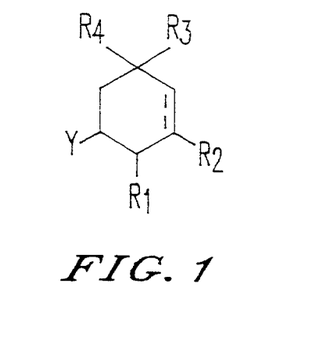
FIG. 1 is a diagrammatic representation of the generalized structure of one class of cyclic anti-tumor promoter compounds of the present invention.
Figure 2:
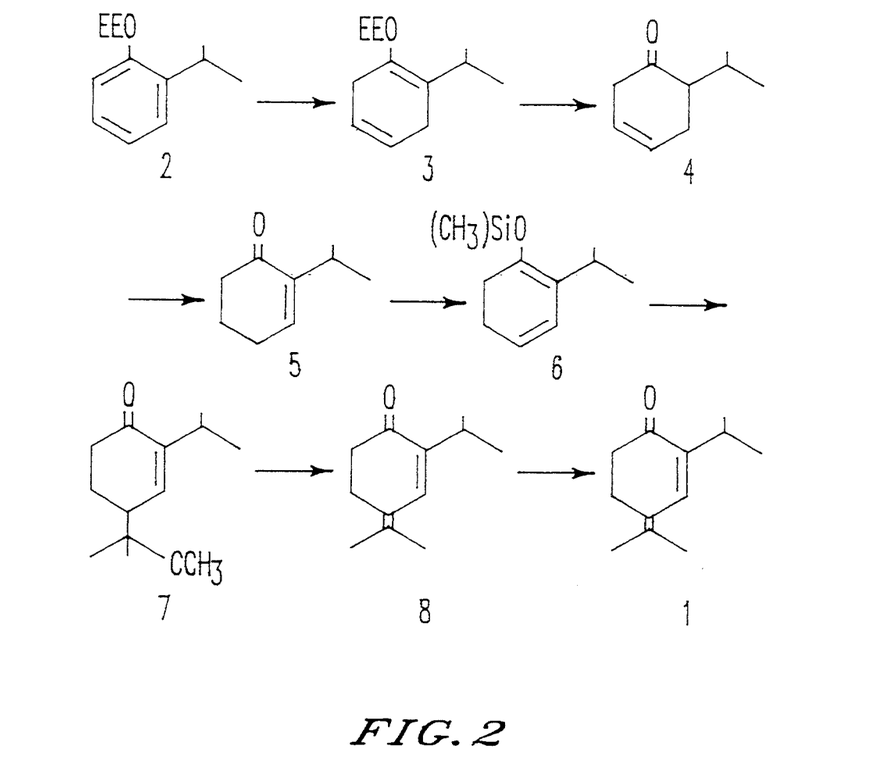
FIGS. 2 through 7 are diagrammatic representations of "flowchart" synthetic protocols for selected compounds of the present invention.
Figure 3:
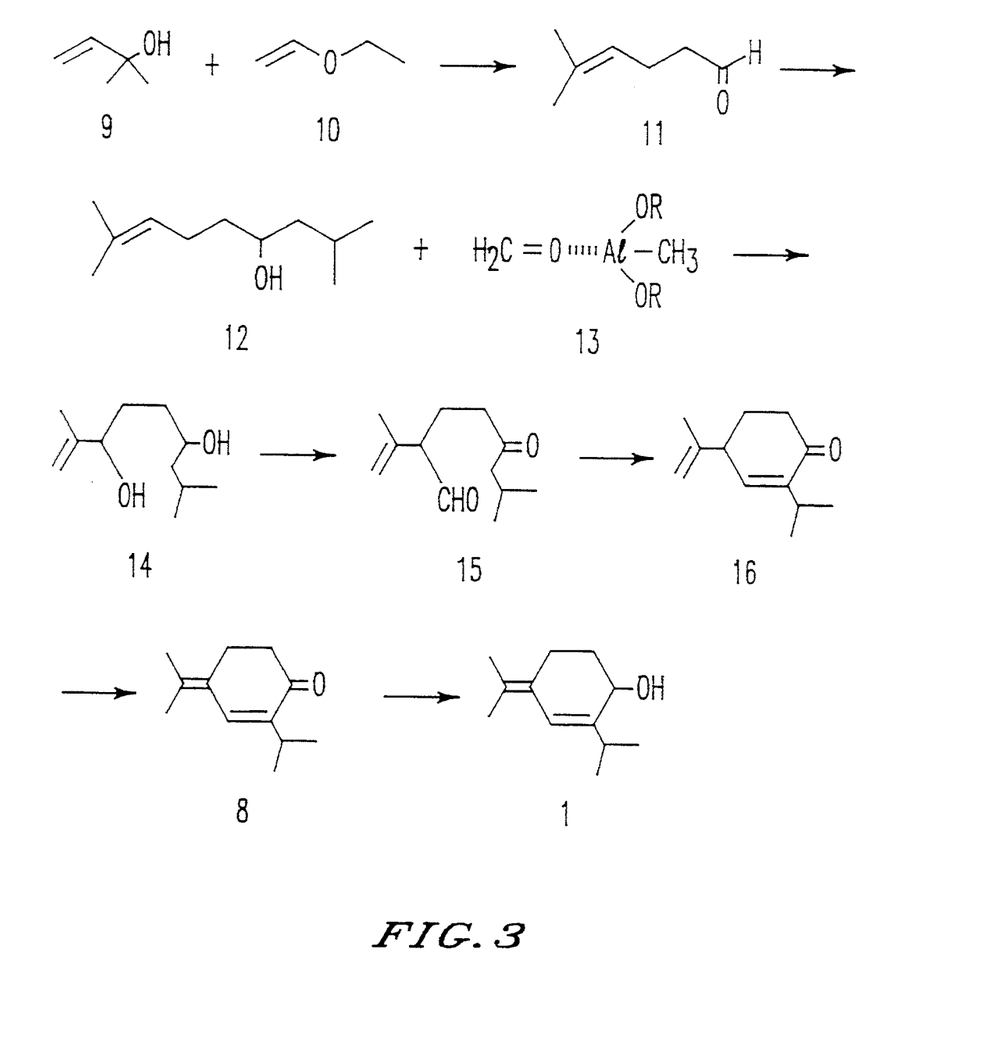

Cyclic anti-tumor promoter compounds within the scope of the invention can be produced in accordance with general principles of chemical synthesis well known in the art. For example, numerous procedures for synthesizing compounds of the class described in Formula II can be developed from general methods for the preparation of six-membered rings, as exemplified in FIGS. 2, 3 and 4, depicting the synthesis of compound 1.

One method for synthesizing aliphatic six-membered carbocyclic molecules is to make use of commercially available aromatic compounds as starting materials. FIG. 2 summarizes such an approach to synthesize 1 which starts with 2-isopropyl phenol. Conversion of the free phenol to the ethoxyethyl ether produces 2, which is reduced to cyclohexadiene 3 with alkali metal in liquid ammonia [Harvey, R. G., Synthesis: 161 (1970)]. Aqueous acidic hydrolysis produces enone 4 which is converted to thermodynamically favored enone 5 by exposure to rhodium trichloride in ethanol [Grieco, P. A., et al., J. Am. Chem. Soc. 98:7102 (1976)]. The trimethylsilyl enol ether [Krafft, M. E. and R. A. Holton, J. Org. Chem. 49:3369 (1984)] is an ambident nucleophile. Electrophilic addition will take place at the unhindered gamma carbon selectively. Exposure of 6 to 2,2-dimethoxypropane and Lewis acid will lead to 7 [Mukaiyama, T. and M. Hayashi, Chemistry Lett.: 15 (1974)]. Upon prolonged exposure to acid, 7 will undergo elimination to dienone 8. Ketone reduction with sodium borohydride leads to 1.

A second general method for the synthesis of aliphatic six-membered rings, and enones in particular, is by means of an aldol-dehydration reaction. FIG. 3 summarizes a synthesis of 1 based upon this strategy. Commercially available 2-methyl-3-buten-1-ol 9 is known to undergo acid-catalyzed condensation with ethyl vinyl ether 10 to produce unsaturated aldehyde 11 [Helv. Chim. Acta 50:2095 (1967)]. Isobutylmagnesium bromide adds to the carbonyl group to produce secondary alcohol 12. The aluminum catalyzed ene reaction of formaldehyde will produce diol 14. Reagent 13 (R=2,6-diphenyl phenol) has been recently described [Maruoka, K., et al., J. Am. Chem. Soc. 112:7422 (1990)], and is known to mediate extremely efficient transformations of the type 12→14. It may be necessary to protect the alcohol group in 12. Alternatively, it may be possible to use the free hydroxyl in 12 for an intramolecular variant of the reaction in which one of the OR groups on aluminum corresponds to 12. Simultaneous oxidation of both hydroxyl groups in 14 will lead to ketoaldehyde 15, the substrate for the intramolecular aldoldehydration. Exposure of 15 to methanolic base will lead to 16, which upon prolonged exposure to base or acid will be converted to the thermodynamically favored isomer 8. Carbonyl reduction, as before, leads to 1.

Figure 4:
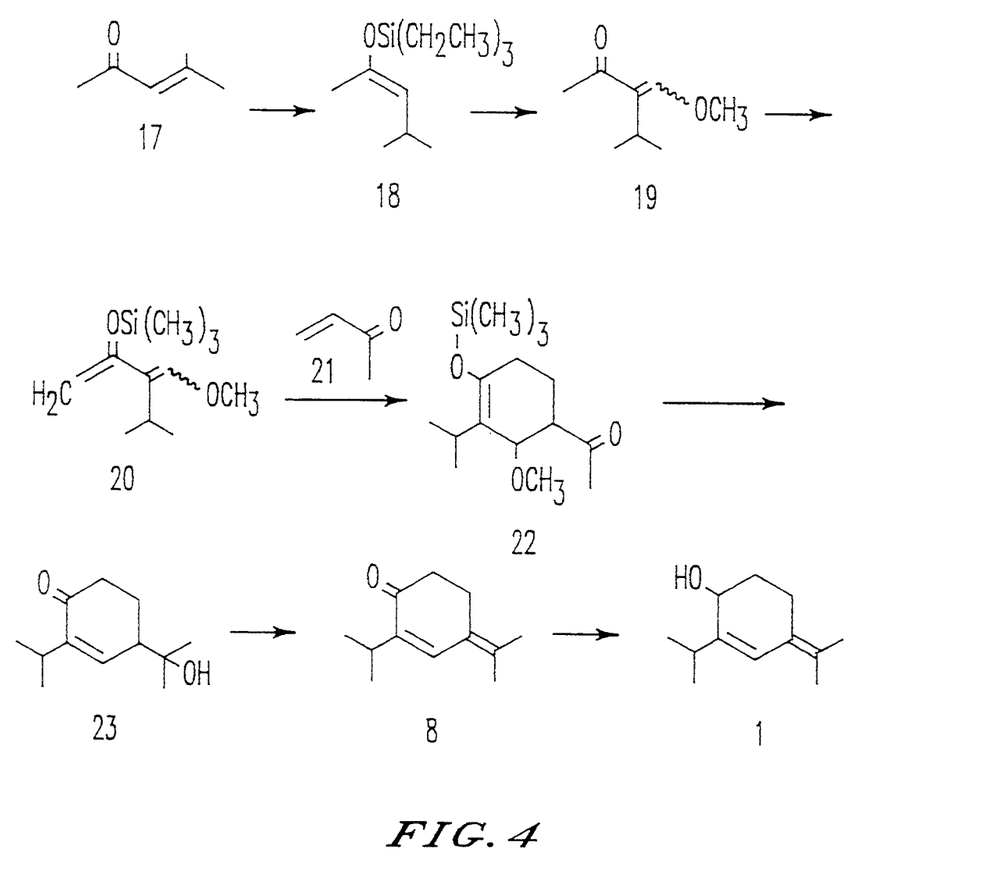

A third approach to the chemical synthesis of six-membered carbocycles such as 1, as depicted in FIG. 4, is by means of a Diels-Alder reaction. Commercially available mesityl oxide 17 can be converted to silyl enol ether 18 by means of a catalytic hydrosilylation reaction with triethylsilane and Wilkinson's catalyst [Ojima, I. et al., J. Organomet. Chem., 94:449 (1975)]. Exposure of 18 to trimethyl orthoformate and titanium tetrachloride produces, upon warming, vinylogous methyl ester 19 as a mixture of geometrical isomers [Murata, S. et al., J. Am. Chem. Soc., 102:3248 (1980)]. The conversion of 19 produces doubly activated diene for the Diels-Alder reaction. Combination of 20 with methyl vinyl ketone 21 produces Diels-Alder product 22, which is immediately treated with methylmagnesium chloride, followed by aqueous acid, to produce enone 23. Acid-catalyzed dehydration of 23 produces dienone 8 which is reduced to 1.

Figure 5:
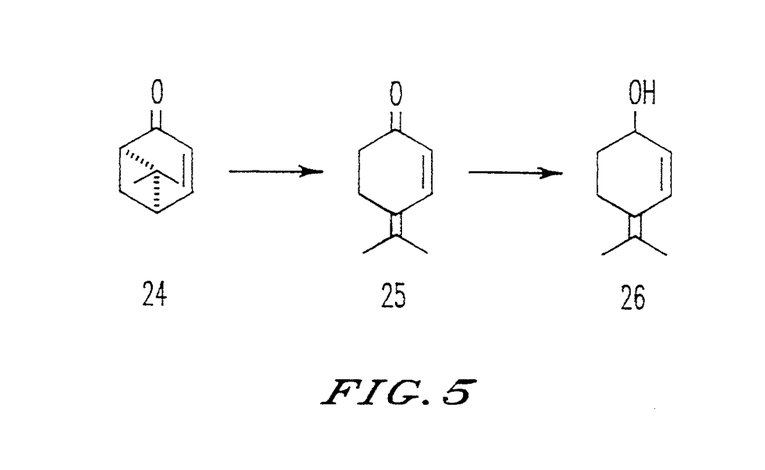

There are three representative synthetic protocols which can be used to prepare 1, and also, by trivial modification, other members of the first class of the present compounds (e.g. FIG. 5). There are many alternatives to the schemes depicted, as well as syntheses which combine elements of all three approaches, which are within the capabilities of one having oridinary skill in the art of chemical synthesis. Nothing in the above discussion should be construed to imply that these are the only methods for the preparation of compounds of this class.

Figure 6:
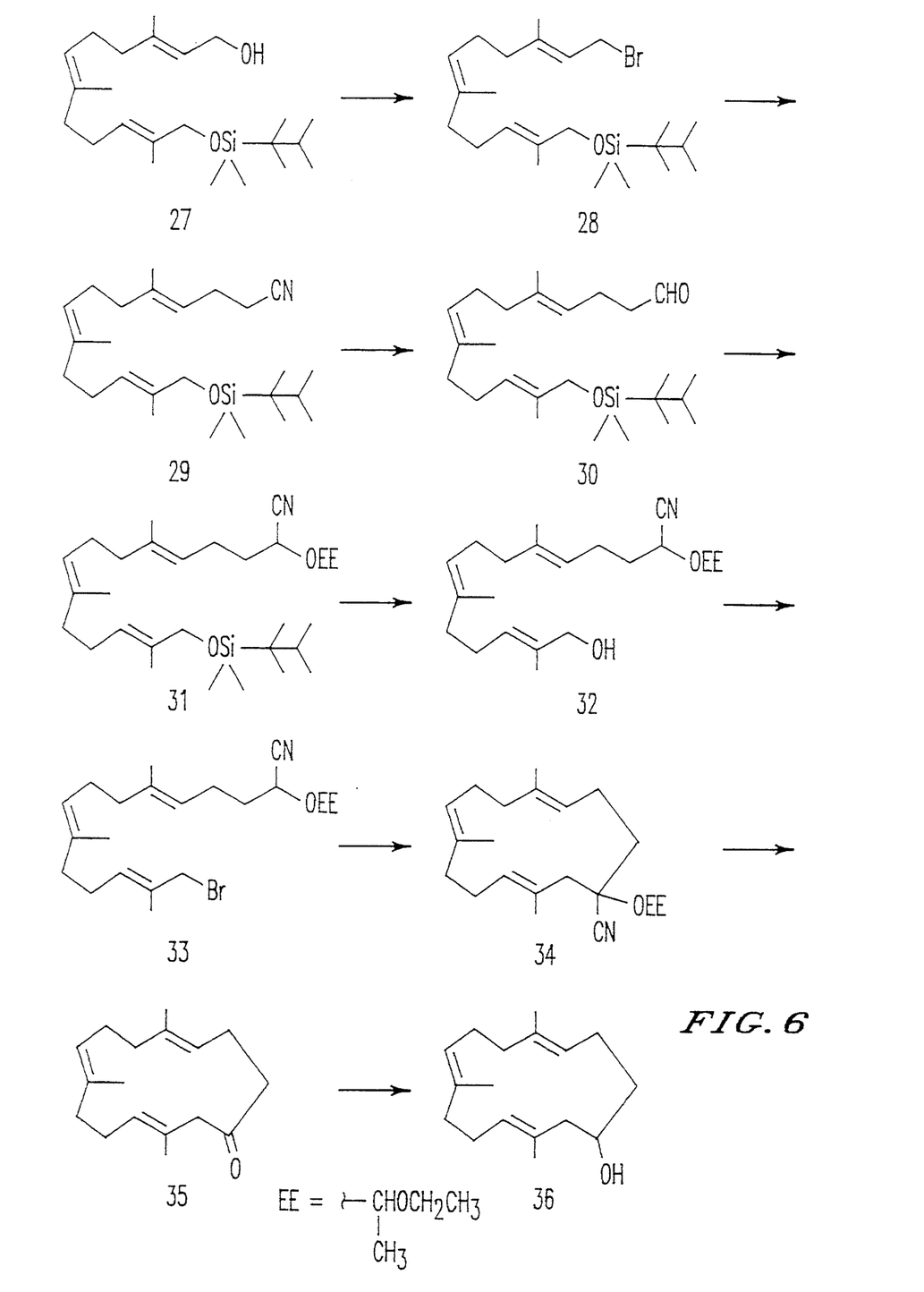
Figure 7:
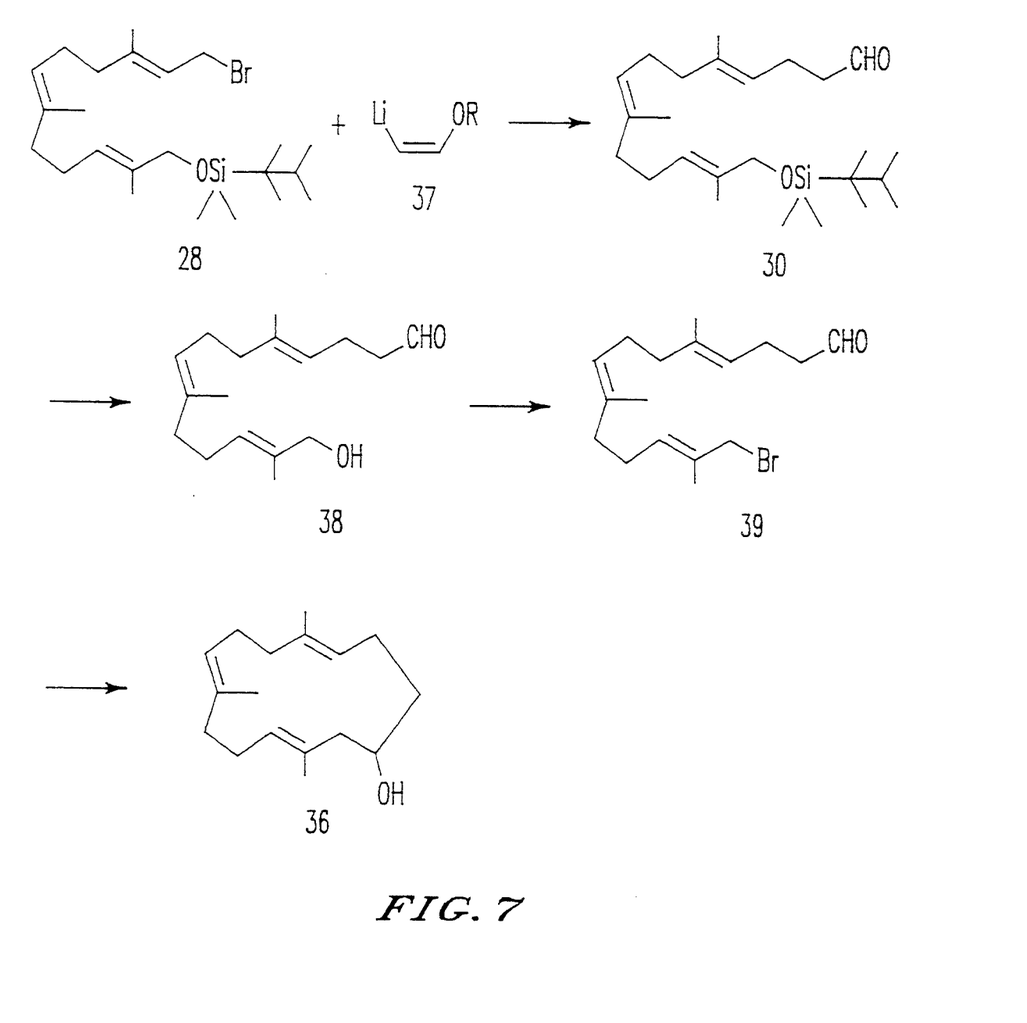

In addition, numerous procedures for synthesizing compounds of the class described in Formula IV can be developed from general methods for the preparation of carbocyclic structures, as disclosed in FIGS. 6 and 7, exemplifying the synthesis of compound 36.

One method for synthesizing aliphatic 14-membered carbocyclic molecules involves the cyclization of anions derived from cyanohydrin ethers, as depicted in FIG. 7 and further described below.

Monosilyl ether 27 is easily prepared from commercially available trans, trans-farnesol. This linear molecule contains all but two of the carbon atoms of the 14-membered ring periphery, and also the three trisubstituted alkenes, each with the appropriate geometry. Conversion of the primary allylic alcohol group in 27 to the bromide takes place by exposure to mesyl chloride and lithium bromide in dimethylformamide [Collington, E. W. and A. I. Meyers, J. Org. Chem., 36:3044 (1971)]. Deprotonation of acetonitrile with n-butyllithium and treatment of the anion with cuprous iodide generates a nucleophile [Corey, E. J. and I. Kuwajima, Tetrahedron Lett., 12:487 (1971)] which displaces the allylic bromide in 28 to produce nitrile 29. Reduction of 29 with diisobutylaluminum hydride in ether at −78° C. [Marshall, J. A. et al., J. Org. Chem., 53:1616 (1988)] gives aldehyde 30. This aldehyde is converted to the corresponding protected cyanohydrin 31 in a three-step, one-pot procedure [Gassman, P. G. and J. J. Talley, Tetrahedron Lett., 19:3773 (1978); Broka, C. A. et al., J. Org. Chem., 53:1584 (1988)]. Exposure of 30 to trimethylsilyl cyanide and zinc iodide produces initially a trimethylsilyl protected cyanohydrin. Selective cleavage of the trimethylsilyl group is accomplished at pH 7 with tetra-n-butylammonium fluoride/acetic acid in tetrahydrofuran. This provides the aldehyde cyanohydrin, which is converted to the ethoxyethyl ether in a subsequent step by exposure to ethyl vinyl ether and pyridinium tosylate. Cleavage of the thexyldimethylsilyl group is accomplished with tetra-n-butylammonium fluoride in tetrahydrofuran at room temperature, providing allylic alcohol 32. The conversion of 32 to bromide 33 is accomplished via the same protocol as for the conversion of 27 to 28. The key reaction of this sequence, the closure of the 14-membered ring, is performed in refluxing tetrahydrofuran in the presence of strong base, providing protected cyanohydrin 34 [Tsuji, J. et al., Tetrahedron Lett., 24:3489 (1983)]. The conversion of the cyanohydrin to ketone 35 takes place in a two-operation, one-pot procedure: hydrolysis of the ethoxyethyl group with pyridinium tosylate, followed by exposure to aqueous sodium hydroxide. Reduction of the carbonyl group in 35 with sodium borohydride provides the cyclic antitumor promoter 36.

A more efficient alternative synthesis of 36 can also be envisioned, as depicted in FIG. 7 and summarized below. Intermediate 28 can be treated with the known lithio anion 37 to produce, after hydrolysis of the enol ether group during workup, aldehyde 30. Removal of the silyl ether protecting group from 30 with tetra-n-butylammonium fluoride gives hydroxyaldehyde 38, from which bromide 39 can be prepared by exposure to mesyl chloride and lithium bromide. Bromide 39 is converted to antitumor promoter 36 in a single step by exposure to chromous chloride [Still, W. C. and D. Mobilio, J. Org. Chem., 48:4785 (1983)].

As was the case with compounds of the first class, numerous alternatives to these schemes, as well as syntheses which combine elements of both approaches, can be envisioned for this class of compounds as well. Nothing in the above discussion should be construed to imply that these are the only methods for the preparation of compounds of this class.

Also provided in accordance with aspects of the invention are pharmaceutical compositions useful as anti-cancer and cancer-prevention agents, which compositions contain the above-recited cyclic anti-tumor promoter compounds together with a pharmaceutically acceptable carrier. Administration of therapeutically effective doses of these compositions can provide effective delivery of the above-recited biological activities to mammalian hosts.

These cyclic anti-tumor promoter compositions are found to be effective in preventing and reversing neoplasms. The cyclic anti-tumor promoter compositions are generally employed either prophylactically or therapeutically.

Compounds and compositions of the present invention which are shown to have the above recited physiological effects can find use as therapeutic agents in the prevention and treatment of various disorders such as, for example, cancer.

Thus, a further aspect of the present invention provides compositions containing a therapeutically effective amount of at least one cyclic anti-tumor promoter compound of the present invention, including the non-toxic addition salts thereof, which may, alone, serve to provide the above-recited therapeutic benefits. Such compositions can also be provided together with physiologically tolerable liquid, gel or solid carriers, diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 $\mu$g/kg, more usually 0.01 to 100 $\mu$g/kg, of the host body weight. Alternatively, dosages within these ranges can be administered by constant infusion over an extended period of time, usually exceeding 24 hours, until the desired therapeutic benefits have been obtained.

The cyclic anti-tumor promoter compounds may be formulated into the therapeutic compositions as neutral or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups (for example in a protonated Schiff base) and will generally be formed with inorganic acids such as, for example, hydrochloric or phosphoric acids, or organic acids such as acetic, oxalic, tartaric, mandelic, and the like.

Such compositions are typically prepared as oral formulations, either as liquid solutions or suspensions, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiological tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

The compositions are conventionally administered orally, for example in an acceptable carrier and, optionally, including flavorings. Alternatively, the compositions are administered parenterally, by injection, for example, either subcutaneously or intravenously. Additional formulations which are suitable for other modes of administration, such as topical administration, include salves, tinctures, creams, lotions, sprays, suppositories, and, in some cases, intranasal aerosols. For salves and creams, traditional binders, carriers and excipients may include, for example, polyalkylene glycols or triglycerides; such salves and creams may be formed from mixtures containing the active ingredient in the range of 0.05% to 5.0%, preferably about 0.1% to 2%.

The following examples serve to illustrate certain preferred embodiments and aspects of the present invention and are not to be construed as limiting the scope thereof.

Experimental

The following examples demonstrate the preparation of precursors to synthesis of cyclic anti-tumor promoter compounds, the synthesis of cyclic anti-tumor promoter compounds of the two disclosed classes, the preparation of compositions containing such compounds and their use as therapeutic agents in accordance with the invention.

In the experimental disclosure which follows, all weights are given in grams (g), milligrams (mg), micrograms (µg) or moles (mol), all concentrations are given as percent by volume (%), molar (M), millimolar (mM) or micromolar (µM), and all volumes are given in liters (L) or milliliters (mL), unless otherwise indicated.

Examples 1 and 2 demonstrate the synthesis of a first class of cyclic anti-tumor promoter compounds in accordance with the present invention: Aliphatic six-membered carbocyclic molecules. In these examples, reference will be made to various compounds depicted in the Figures by resort to the corresponding reference numerals.

Example 1

The cyclic anti-tumor promoter compound of the invention identified by the formula:

is prepared from 2-Isopropylcyclohexenone in accordance with the present disclosure, with particular reference to FIG. 2.

General. Ethyl ether and tetrahydrofuran (THF) were distilled from a purple solution of sodium benzophenone ketyl. Chlorotrimethylsilane, hexamethylphosphoric triamide (HMPA) and triethylamine were distilled freshly from calcium hydride. Dichloromethane was distilled from phosphorus pentoxide.

Preparation of trimethylsilyl enol ether 6

2-Isopropylcyclohexenone 5 was prepared from o-anisic acid according to the procedure of Taber (Taber, D. F., J. Org. Chem., 41:2649 (1976)). An ethereal solution of 357 mg (1.1 equiv, 2.2 mmol) of anhydrous ferric chloride in 15 mL of ether at 0° C. was slowly treated with 2.2 mL (3.3 equiv, 6.6 mmol) of a 3.0M ethereal solution of methylmagnesium bromide. The resulting slurry was stirred at 25° C. for 1 h, then 276 mg (2.0 mmol) of 5 dissolved in 5 mL of ether was slowly added during 10 min. After 30 min, 0.84 mL (3.3 equiv, 6.6 mmol) of chlorotrimethylsilane, 0.95 mL (3.4 equiv, 6.8 mmol) of triethylamine and 0.38 mL (1.1 equiv, 2.2 mmol) of HMPA were added in that order. The solution was stirred overnight and was diluted with 10 mL of ethyl ether. The mixture was poured onto cold (0° C.) saturated sodium bicarbonate solution and the aqueous phase was extracted with 15 mL ether. The organic phase was dried over anhydrous sodium sulfate and was concentrated. The resulting colorless oil was filtered through a short plug of silica gel, using 5% ethyl acetate in hexane as the eluant, in order to remove traces of triethylamine and HMPA. The eluant was concentrated to produce a colorless oil which was used immediately and without further purification in the following reaction.

Preparation of enone 7

A solution of 1.0 mmol (1.0 equiv) of titanium tetrachloride in 10 mL of dichloromethane was cooled to −78° C. and was treated dropwise with 0.12 mL (1.0 equiv, 1.0 mmol) of 2,2-dimethoxypropane. After 5 min, 210 mg (1.0 mmol) of trimethylsilyl enol ether 6, dissolved in 5 mL of dichloromethane, was added. The resulting deep red solution was stirred for 30 min, then 5 mL of water was added and the mixture was warmed to 25° C. The aqueous layer was extracted twice with 10 mL of dichloromethane. The organic layer was dried over anhydrous magnesium sulfate and was concentrated. The oily residue was purified by flash column chromatography on silica gel, using 10% ethyl acetate in hexane as the eluant, to produce 126 mg (60% yield) of enone 7 and 58 mg (40% yield) of 2-isopropylcyclohexenone 5. Enone 7: ir (neat) 3020, 1680, 1450, 1370, 1050 cm$^{-1}$; $^1$H nmr (300 MHz, CDCl$_3$) 6.75 (s, 1H), 3.25 (s, 3H), 2.87 (dq, J=6.9, 6.6 Hz, 1H), 2.63–2.50 (m, 2H), 2.38–2.26 (m, 1H), 2.03–1.96 (m, 1H), 1.71–1.56 (m, 1H), 1.17 (s, 3H), 1.10 (s, 3H), 1.02 (d, J=6.9 Hz, 3H), 0.99 (d, J=6.6 Hz, 3H).

Preparation of dienone 8

To a solution of 294 mg (1.4 mmol) of 7 in 12 mL of 2,2,2-trifluoroethanol was added slowly at 25° C. 0.88 mL (14.0 mmol, 10.0 equiv) of 70% aqueous perchloric acid. The solution was heated at 35°–40° C. for 30 h, then 10 mL of water was added. The mixture was extracted twice with 10 mL of ether, the organic phase was dried over anhydrous magnesium sulfate and concentrated. The oily residue was purified by flash column chromatography on silica gel, using 5% ethyl acetate in hexane as the eluant, to produce 120 mg (45% yield) of 8, 45 mg (25% yield) of 2,4-diisopropylphenol and 63 mg (30% yield) of starting material 7. Dienone 8: ir (neat) 3020, 1670, 1450, 1380 cm$^{-1}$; $^1$H nmr (300 MHz, CDCl$_3$) 7.24 (s, 1H), 2.97 (dq, J=6.9, 6.6 Hz, 1H),

2.66 (t, J=6.9 Hz, 2H), 2.46 (dd, J=7.5, 6.6 Hz, 2H), 1.93 (s, 3H), 1.87 (s, 3H), 1.07 (s, 3H), 1.04 (s, 3H).

Reduction of 8 to produce 1

A solution of 100 mg (0.56 mmol) of 8 in 5 mL of methanol at 25° C. was treated with 138 mg (1.0 equiv, 0.56 mmol) of ceric chloride. After 5 min, 22 mg (1.0 equiv, 0.56 mmol) of sodium borohydride was added, the solution was stirred for 2 min and water was added. The reaction mixture was extracted twice with 10 mL of ether. The organic phase was dried over anhydrous sodium sulfate and was concentrated. The residue was purified by flash column chromatography, using 10% ethyl acetate in hexane as the eluent, to produce 98 mg (96% yield) of 1 as a low melting crystalline solid: ir (neat) 3300, 1450, 1380 cm$^{-1}$; $^1$H nmr (300 MHz, CDCl$_3$) 6.31 (s, 1H), 4.24 (dd, J=6.9, 6.6 Hz, 1H), 2.52 (dq, J=6.9, 6.6 Hz, 1H), 2.37 (m, 2H), 1.81-1.76 (m, 8H), 1.11 (t,J=7.2 Hz, 6H); $^{13}$C nmr (75 MHz, CDCl$_3$) 144.47, 127.57, 126.76, 120.88, 65.95, 32.43, 31.79, 22.59, 21.64, 21.32, 20.86, 19.68.

Example 2

The cyclic anti-tumor promoter compound of the invention identified by the formula:

is prepared from cyclohexenone 24 in accordance with the present disclosure, with particular reference to FIG. 5.

Rearrangement of enone 24 to dienone 25

A solution of 408 mg of enone 24 in 25 mL of 1:1 water/2,2,2-trifluoroethanol was treated with 2 mL of conc. perchloric acid at reflux for 44 h. The reaction mixture was cooled to 25° C. and was extracted with 225 mL ether. The ethereal phase was washed with saturated sodium bicarbonate, followed by water and brine, and was dried over anhydrous magnesium sulfate. Evaporation of the solvent gave 403 mg of crude product which was used for the following reaction without further purification. Dienone 25: $^1$H nmr (300 MHz, CDCl$_3$) 7.47 (d, J=10.0 Hz, 1H), 5.83 (d, J=10.0 Hz, 1H), 2.71 (t, J=7.2 Hz, 2H), 2.46 (t, J=7.2 Hz, 2H), 1.93 (s, 3H), 1.89 (s, 3H).

Reduction of dienone 25 to alcohol 26

A solution of 403 mg of dienone 25 was added to a suspension of 3.6 g (3.4 equiv) of ceric chloride hydrate [Coxon, J. M. et al., Tetrahedron, 41:5213 (1981); Gemal, A. L. and J. L. Luche, J. Am. Chem. Soc., 103:5454 (1981)] in 15 mL of methanol at 0° C. 132 mg (1.1 equiv) of sodium borohydride was added and the reaction was stirred for 15 min. Ice water was added to quench the reaction and stirring was continued for 10 min at 0° C. The reaction mixture was extracted with ethyl acetate, and the organic phase was organic phase was washed with brine and dried over anhydrous magnesium sulfate. Solvent evaporation in vacuo, followed by flash column chromatography of the residue, using 15% ethyl acetate in hexane containing 1% diisopropylamine as the eluent, produced 169 mg (42% yield) of 26: ir (neat) 3380, 3040, 2920, 1640, 1440, 1375, 1050 cm$^{-1}$H nmr (300 MHz, C$_6$D$_6$) 6.56 (br d, J=10.0 Hz, 1H), 5.82 (d, J=10.0 Hz, 1H), 4.27 (br s, 1H), 2.46 (m, 1H), 2.16 (br t, J=12.1 Hz, 1H), 1.89 (m, 1H), 1.72 (s, 3H), 1.69 (m, 1H), 1.65 (s, 3H).

Example 3 demonstrates the synthesis of a second class of cyclic anti-tumor promoter compounds in accordance with the present invention: Aliphatic 14-membered carbocyclic molecules. In these examples, reference will be made to various compounds depicted in the Figures by resort to the corresponding reference numerals.

Example 3

The cyclic anti-tumor promoter compound of the invention identified by the formula:

is prepared from trans, trans-farnesyl acetate (as the precursor to alcohol 27) in accordance with the present disclosure, with particular reference to FIG. 6.

Preparation of allylic bromide 28 from alcohol 27

Alcohol 27 (750 mg, 1.97 mmol) was dissolved in 20 mL of dry N,N-dimethylformamide (DMF) and was cooled to 0° C. 2,6-Lutidine (2.0 equiv, 0.46 mL) and lithium bromide (7.0 equiv, 1.2 g) were added to the yellow solution and stirred for 10 min. Mesyl chloride (1.5 equiv., 0.23 mL) was added dropwise and the solution was stirred for 1 h. Ice and hexane were added and the solution extracted three times with hexane. The combined hexane extracts were dried over anhydrous magnesium sulfate and the solvent was removed under reduced pressure. Purification of the crude material by flash column chromatography, using 5% ethyl acetate in hexane as the eluent, produced bromide 28 (734 mg, 84% yield) as a clear yellow oil: ir (neat) 2950, 1460, 1380, 1260, 660 cm$^{-1}$; $^1$H nmr (300 MHz, CDCl$_3$) 5.44 (t, J=6.9 Hz, 1H), 5.37 (m, 1H), 5.11 (m, 1H), 4.10 (d, J=8.1 Hz, 2H), 4.00 (s, 2H), 2.2-1.9 (m, 8H), 1.73 (s, 3H), 1.60 (s, 3H), 1.55 (s, 3H), 1.26 (m, 1H), 0.90 (s, 6H), 0.88 (s, 3H), 0.86 (s, 3H), 0.09 (s, 6H).

Preparation of nitrile 29 from bromide 28

To 20 mL of tetrahydrofuran (THF) was added acetonitrile (8.0 equiv, 0.4 mL) and the solution was cooled to −78° C. n-Butyllithium (6.0 equiv, 2.29M, 3.0 mL) was added dropwise and the solution was stirred for 1 h. The solution was warmed to −20° C. and cuprous iodide (8.0 equiv, 1.72 g) was added. After stirring for 20 min., 500 mg (1.13 mmol) of bromide 28 was added in 10 mL THF and the solution was allowed to warm to room temperature over a 2 h period. Saturated aqueous ammonium chloride was added and the mixture was extracted three times with ether. The combined ether extracts were dried over anhydrous magnesium sulfate and the solvents were removed under reduced pressure. Purification of the residue by flash column chromatography, using 10% ethyl acetate in hexane as the eluent, gave nitrile 29 (368 mg, 81% yield) as a clear oil: ir (neat) 2950, 2240, 1460, 1380, 1260, 1080 cm$^{-1}$; $^1$H nmr (300 MHz, CDCl$_3$) 5.36 (t, J=6.9 Hz, 1H), 5.12 (m, 2H), 3.98 (s, 2H), 2.35 (m, 2H), 2.2–1.9 (m, 10H), 1.65 (s, 3H), 1.59 (s, 3H), 1.55 (s, 3H), 1.26 (m, 1H), 0.90 (s, 6H), 0.88 (s, 3H), 0.86 (s, 3H), 0.09 (s, 6H).

Reduction of 29 to aldehyde 30

A solution of 300 mg (0.74 mmol) of nitrile 29 in 5 mL of anhydrous ether was treated with 1.1 mL (1.0M, 1.5 equiv) of diisobutylaluminum hydride solution at −78° C. After 30 min., the solution was warmed to 0° C. during 30 min. The solution was quenched with saturated aqueous Rochelle salt and was extracted three times with ether. The combined ethereal extracts were dried over anhydrous magnesium sulfate and the solvent was removed under reduced pressure. The residue was purified by flash column chromatography on silica gel, using 10% ethyl acetate in hexane as the eluent, to produce 257 mg (85% yield) of aldehyde 30: ir (neat) 2950, 1730, 1460, 1380, 1260, 1080 cm$^{-1}$; $^1$H nmr (300 MHz, CDCl$_3$) 9.76 (t, J=1.6 Hz, 1H), 5.36 (t, J=6.6 Hz, 1H), 5.10 (m, 2H), 3.97 (s, 2H), 2.46 (dt, J=7.0, 1.5 Hz, 2H), 2.34 (t, J=7.2 Hz, 2H), 2.18–1.95 (m, 8H), 1.66 (s, 3H), 1.63 (s, 3H), 1.59 (s, 3H), 1.26 (m, 1H), 0.90 (s, 6H), 0.88 (s, 3H), 0.86 (s, 3H), 0.09 (s, 6H).

Protected cyanohydrin 31 from aldehyde 30

A solution of 300 mg (0.75 mmol) of aldehyde 30 in 10 mL of anhydrous dichloromethane at 0° C. was treated with 24 mg (0.1 equiv) of anhydrous zinc iodide. The solution was allowed to warm to room temperature and was stirred overnight. The dichloromethane was removed under reduced pressure and the residue was dissolved in 10 mL of THF and cooled to −78° C. A buffered solution of tetra-n-butylammonium fluoride and acetic acid (0.23 mL, pH 7, 1M in THF) was added dropwise. The reaction was quenched with water after stirring for 30 min and the solution was extracted with ether three times. The combined ether extracts were combined, dried over anhydrous magnesium sulfate, and the solvent was removed under reduced pressure. The crude cyanohydrin was dissolved in 5 mL of dichloromethane and 0.5 mL of ethyl vinyl ether and 20 mg (0.1 equiv) of pyridinium tosylate were added at room temperature. The reaction was quenched after 30 min with water, the mixture was extracted three times with dichloromethane and the combined extracts were dried over anhydrous magnesium sulfate. The solvent was evaporated and the crude material was purified by flash column chromatography, using 10% ethyl acetate in hexane as the eluent. Protected cyanohydrin 31 was isolated as a mixture of diastereoisomers (due to the asymmetric center on the protecting group) in 51% overall yield from 30 (190 mg). Cyanohydrin 31: ir (neat) 2950, 2220, 1460, 1380, 1260, 1080 cm$^{-1}$; $^1$H nmr (300 MHz, CDCl$_3$) 5.38 (m, 1H), 5.10 (m, 2H), 4.93 (q, J=5.4 Hz, 1H), 4.82 (m, 1H), 4.47 (t, J=6.6 Hz, 1H), 4.27 (m, 1H), 3.99 (s, 2H), 3.73–3.40 (m, 2H), 2.2–1.8 (m, 12H), 1.69 (s, 3H), 1.66 (s, 3H), 1.62–1.60 (m, 6H), 1.50–1.20 (m, 4H), 0.90 (s, 3H), 0.88 (s, 3H), 0.86 (s, 3H), 0.09 (s, 6H).

Desilylation of 31; preparation of allylic alcohol 32

A solution of 150 mg (0.30 mmol) of silyl ether 31 in 5 mL of THF was treated with 2 equiv (0.19 mL of 1M) of tetra-n-butylammonium fluoride dropwise at room temperature. The reaction was quenched with water after 1 h and the solution was extracted with ether three times. The combined ether extracts were dried over anhydrous magnesium sulfate and the solvent was removed under reduced pressure. The product was purified by flash column chromatography on silica gel, using 15% ethyl acetate in hexane as the eluent, to give 87 mg (81% yield of the pure product as a mixture of diastereomers. Alcohol 32: ir (neat) 3450, 2950, 2220, 1460, 1380, 1080 cm$^{-1}$; $^1$H nmr (300 MHz, CDCl$_3$) 5.41 (dt, J=6.8 Hz, 1H), 5.12 (m, 2H), 4.91 (q, J=8.0 Hz, 1H), 4.81 (q, J=8.1 Hz, 1H), 4.46 (t, J=6.7 Hz, 1H), 4.26 (t, J=6.7 Hz, 1H), 3.99 (s, 2H), 3.7–3.5 (m, 2H), 2.24–1.80 (m, 10H), 1.7–1.5 (m, 12H), 1.36 (m, 3H), 1.25 (m, 3H).

Allylic bromide 33

The same procedure as for the conversion of 27 to 28 was followed, using 100 mg of alcohol 32, together with 167 mg (7.0 equiv) of lithium bromide, 0.06 mL of 2,6-lutidine (2.0 equiv) and 0.03 mL of mesyl chloride (1.5 equiv). Bromide 33 was obtained in 83% yield (97 mg) after purification by flash column chromatography, using 10% ethyl acetate in hexane as the eluent. The product was a mixture of diastereomers. Bromide 33: ir (neat) 2950, 2240, 1460, 1380, 1080, 680 cm$^{-1}$; $^1$H nmr (300 MHz, CDCl$_3$) 5.51 (t, J=6.7 Hz, 1H), 5.15 (m, 2H), 4.90 (q, J=7.8 Hz, 1H), 4.80 (q, J=8.1 Hz, 1H), 4.47 (t, J=6.6 Hz, 1H), 4.26 (t, J=6.5 Hz, 1H), 4.05 (s, 2H), 3.7–3.5 (m, 2H), 2.2–1.8 (m, 10H), 1.71 (s, 3H), 1.62–1.5 (s, 9H), 1.36 (m, 3H), 1.25 (m, 3H).

Cyclization to 34

To bromide 33 (50 mg, 0.12 mmol) in 3 mL of THF was added 5 equiv (0.6 mL of 1M in THF) sodium hexamethyldisilylamide at 65° C. dropwise over 5 min. The reaction was quenched after 0.5 h with saturated aqueous ammonium chloride and the mixture was extracted with ether. The combined ether extracts were dried over anhydrous magnesium sulfate and the solvent was removed under reduced pressure. Flash column chromatography, using 5% ethyl acetate in hexane as the eluent, produced 32 mg (80% yield) of the cyclic product 34: ir (neat) 2950, 2220, 1460, 1380, 1060 cm$^{-1}$; $^1$H nmr (300 MHz, CDCl$_3$) 5.12 (m, 3H), 4.92 (m, 1H), 3.7–3.5 (m, 2H), 2.58 (s, 1H), 2.49 (d, J=5.7 Hz, 1H), 2.3–1.8 (m, 12H), 1.74 (d, J=7.8 Hz, 2H), 1.58–1.52 (m, 9H), 1.36 (m, 3H), 1.23 (m, 3H).

Cyclic ketone 35

To 30 mg (0.09 mmol) of 34 was added 5 mL methanol and 2 mg (0.1 equiv) of pyridinium tosylate. The solution was stirred at room temperature for 2 h and 2 mL of 1N aqueous sodium hydroxide was added. The solution was extracted three times with ether and the combined ether extracts were dried over anhydrous magnesium sulfate. Solvent evaporation produced the crude product which was purified by flash column chromatography, using 1% ethyl acetate in hexane as the eluent, to produce 16 mg (75% yield) of ketone 35: ir (neat) 2950, 1710, 1450, 1380 cm$^{-1}$; $^1$H nmr (300 MHz, CDCl$_3$) 5.04 (m, 2H), 4.88 (t, J=6.3 Hz, 1H), 2.93 (s, 2H), 2.52 (m, 2H), 2.3–1.9 (m, 10 H), 1.66 (s, 3 H), 1.58 (s, 3 H), 1.55 (s, 3 H).

Reduction of 35 to 36.

A solution of 15 mg (0.06 mmol) of ketone 35 in 5 mL of methanol at room temperature was treated with 11.5 mg (5 equiv) of solid sodium borohydride. The reaction was quenched with water after 5 min and the solution was extracted three times with ether. The combined ether extracts were dried over anhydrous magnesium sulfate and the solvent was removed under reduced pressure. Purification of the crude product by flash column chromatography, using 1% ethyl acetate in hexane as the eluent, produced 12 mg (80% yield) of alcohol 36: ir (neat) 3350, 2950, 1460, 1380, 1060 cm$^{-1}$; $^1$H nmr (300 MHz, CDCl$_3$) 5.14 (dt, J=7.3, 1.2 Hz, 1 H), 4.98 (m, 2 H), 3.18 (m, 1 H), 2.4–1.9 (m, 14 H), 1.62 (s, 3 H), 1.58 (s, 3 H), 1.56 (s, 3 H).

Following the protocols disclosed above, and as outlined in detail in Examples 1 through 3, with appropriate adjustments being made to produce the desired end product, one will be able to obtain additional cyclic anti-tumor promoter compounds of the present invention.

In order to demonstrate the utility and efficacy of compounds and compositions in accordance with the present invention, the following examples illustrate certain embodiments thereof.

Example 4

A therapeutic composition of the invention adapted for oral administration as a capsule can be prepared from the present cyclic anti-tumor promoter compounds, as follows:

| Ingredient | Per Capsule |
| --- | --- |
| Anti-tumor Promoter Compound | 0.1 mg |
| wax mixture | 50.5 mg |
| vegetable oil | 98.9 mg |
| ethylenediaminetetraacetic acid trisodium salt | 0.5 mg |

Such compositions can be orally administered to mammalian hosts in accordance with the practice of the present invention, thereby obtaining the useful benefits described herein.

Example 5

A therapeutic composition of the invention adapted for topical administration as a salve can be prepared from the present cyclic anti-tumor promoter compounds, as follows:

| Ingredient | Percentage |
| --- | --- |
| Anti-tumor Promoter Compound | 0.1 |
| vaseline white | 35 |
| wax white | 10 |
| paraffin oil viscous | 18 |
| DEHYMULSE E | 7 |
| benzoic acid USP | 0.2 |
| water deionized | ad 100 |

*high molecular weight aliphatic mixed ester (supplied by Henkel)

Such compositions can be topically administered to mammalian hosts in accordance with the practice of the present invention, thereby obtaining the useful benefits described herein.

Example 6

The use of the cyclic anti-tumor promoter compounds and compositions prepared in accordance with Examples 1–5 as anti-neoplasm agents is demonstrated by their ability to supress the promotion of tumor formation by teleocidin in two-stage carcinogenesis in mouse skin.

This evaluation was preformed as follows: The backs of seven week old female CD-1 mice (obtained from Charles River Japan, Inc., Kanagawa, Japan) were shaved to expose the skin and initiation was accomplished with a single application of 50 μg of 7,12-dimethylbenz[a]anthracene (DMBA) dissolved in 0.1 mL acetone.

Thereafter, the compounds to be evaluated were applied, followed in 15 min. by application of 2.5 μg of teleocidin (isolated from Streptomyces mediocidicus in accordance with Fujiki, H. and T. Sugimura, Adv. Cancer Res., 49, 223, 1987) dissolved in 0.1 mL acetone. These treatments were repeated twice a week for 25 weeks.

Figure 8A:
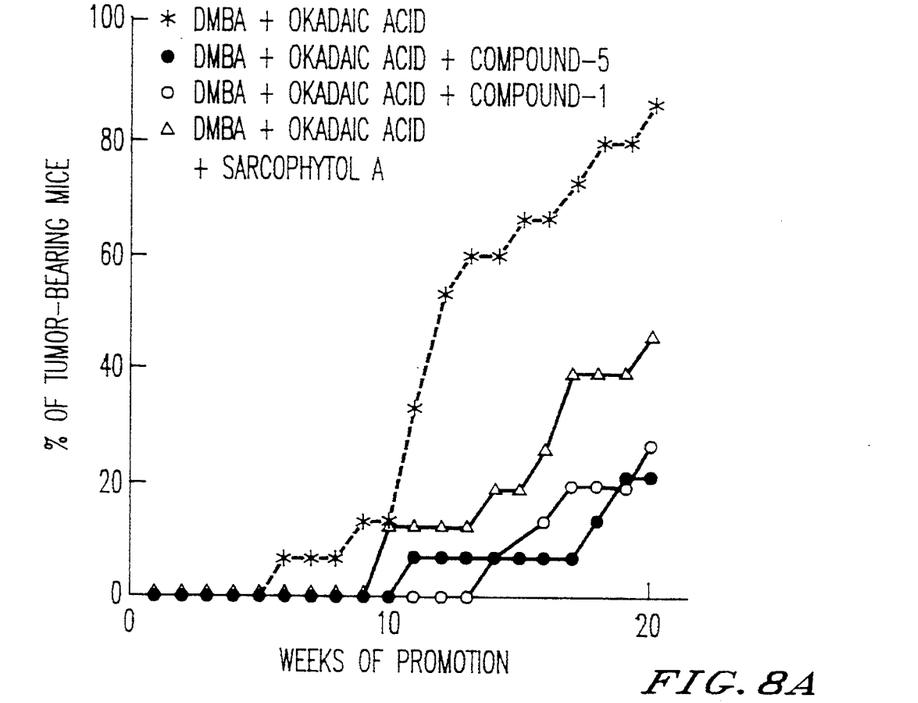
FIG. 8 is a graphic presentation of the anti-tumor promoter activity of selected compounds of the present invention.
Figure 8B:
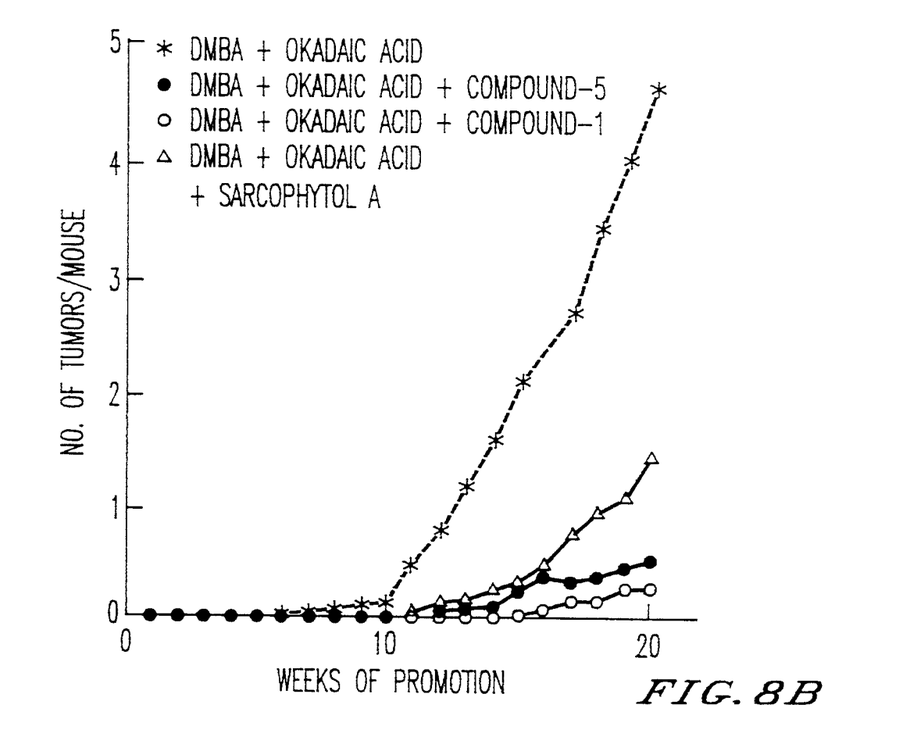

Controls consisted of mice treated with DMBA only and DMBA plus anti-tumor promoter. The results were evaluated as the percentage of tumor-bearing mice and the average number of tumors per mouse. As can be seen in FIG. 8, compounds and compositions produced in accordance with the present invention display anti-tumor promoter activity which equals or exceeds that of sarcophytol A in both the inhibition of tumor promotion and the reduction in the number of tumors produced.

Example 7

The use of the cyclic anti-tumor promoter compounds and compositions prepared in accordance with Examples 1–5 as anti-neoplasm agents is also demonstrated by their ability to inhibit the farnesylation of ras-p21 by ras farnesyl transferase.

This inhibitory activity is assayed using partially purified ras farnesyl transferase obtained from bovine brain by DEA gel filtration (J. Biol. Chem., 260, 15575, 1991) purified to display a single band in gel electrophoresis.

A reaction mixture is prepared by including the test sample in a solution containing 0.67 μM $^3$H-Farnesylpyrophosphate (9.25 kBq), 4 μg ras-p21, 10 μL ras farnesyl transferase, 50 mM Tris-HCl, pH 7.5, 20 mM KCl, 50 μM ZnCl$_2$ and 1 mM Dithiothreitol. This mixture is incubated at 37° C. for 20 minutes. The solutes are then precipitated with trichloroacetic acid (TCA) and the precipitate is filtered on a glass filter. The amount of farnesyl incorporated into the ras-p21 is then determined by liquid scintillation.

The results of these tests are reported as the inhibitory concentration (IC$_{50}$) presented in Table 1.

TABLE 1

| Inhibitory Activity of Synthetic Compounds | |
| --- | --- |
| Compound | IC$_{50}$ Value (μM) |
| COMPOUND 5 | 29 |
| Sarcophytol A | >1,000 |

Figure 9:
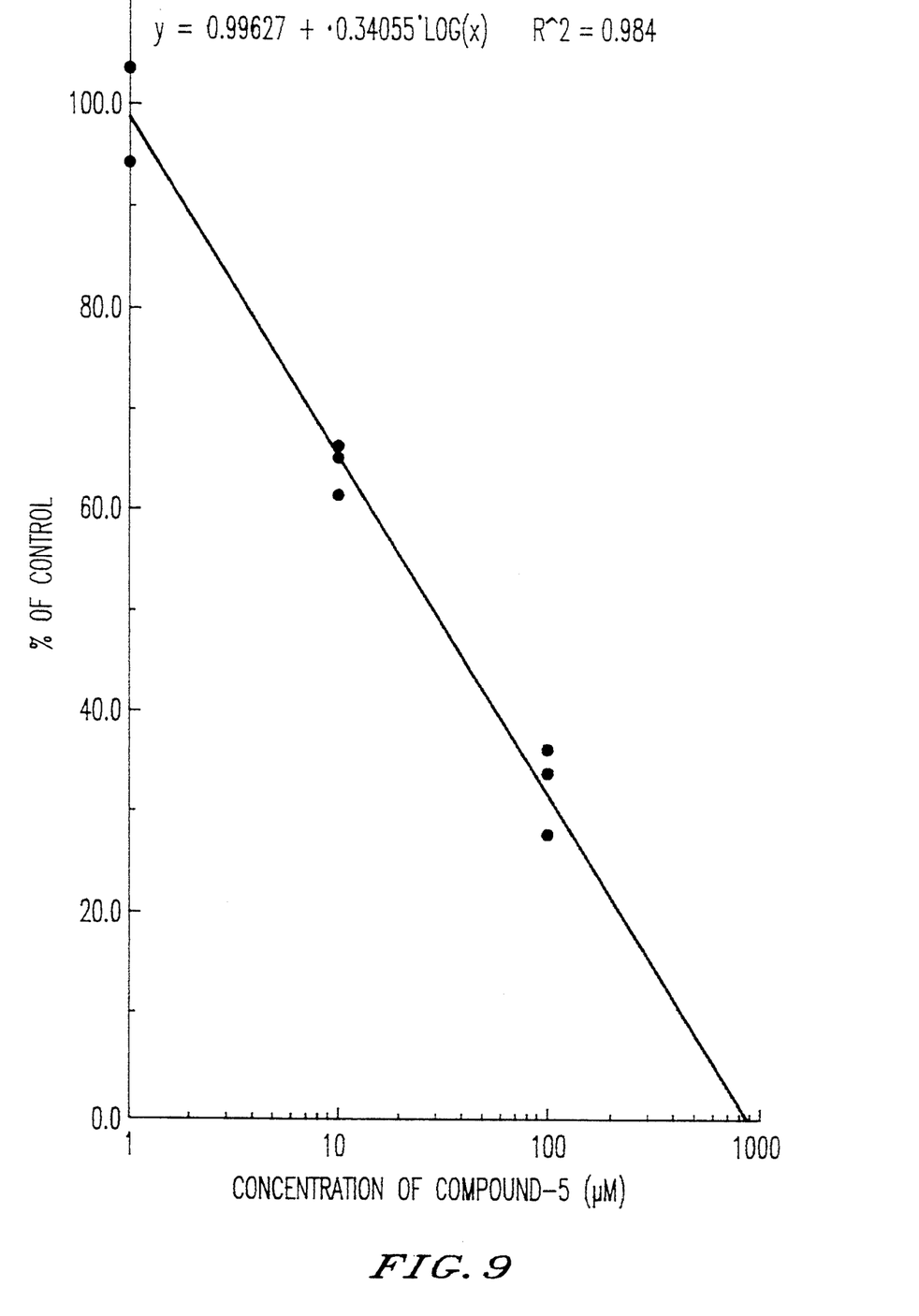
FIG. 9 is a graphic presentation of the farnesylation inhibition activity of selected compounds of the present invention as a function of their concentration.

In addition, FIG. 9 presents a plot of the concentration of COMPOUND 5 versus activity (compared to a control value) demonstrating the dose-dependent activity of this representative compound of the present invention.

From the results disclosed in Examples 6 and 7, it can be seen that although compounds of the present invention are useful as anti-tumor promoters, the mode of action appears different from the natural compound sarcophytol A, which does not appear to be an effective inhibitor of the farnesylation of ras-p21 by ras farnesyl transferase.

Thus it can be seen that the present invention provides novel and improved compounds, compositions and methods for their use as anti-cancer and cancer-prevention agents.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

I claim:

1. A cyclic compound of formula wherein:
the bond between $C_2$ and $C_3$ is a single or a double bond;
$R_1$ is $OR_5$, wherein $R_5$ is H, an alkyl or acyl group having one to six carbon atoms or $CO_2R_6$ wherein $R_6$ is H or an alkyl group having one to six carbon atoms;
$R_2$ is an alkenyl group having one to six carbon atoms;
each of $R_3$ and $R_4$ is independently H, an alkyl or alkenyl group having one to six carbon atoms, or a phenyl group which may be attached via an alkyl or alkenyl group having one to six carbon atoms or a halogen atom, or $R_3$ and $R_4$ may be taken together to form a methylidene, an alkylidene having one to six carbon atoms or an arylidene group; and
Y is H or an O-acyl substituted group.

2. The cyclic compound of claim 1, wherein $R_3$ and $R_4$ are not simultaneously H.

3. The cyclic compound of claim 1, wherein $R_3$ and $R_4$ taken together form a group selected from:

4. The cyclic compound of claim 1, wherein each of $R_3$ and $R_4$ is independently H, an alkyl or alkenyl group having one to six carbon atoms, or a phenyl group which may be attached via an alkyl or alkenyl group having one to six carbon atoms or a halogen atom.

5. The cyclic compound of claim 1, wherein the bond between $C_2$ and $C_3$ is a single bond and $R_2$ is a group selected from:

6. The cyclic compound of claim 1, wherein $R_1$ is $CO_2R_6$ wherein $R_6$ is H or an alkyl group having one to six carbon atoms.

7. The cyclic compound of claim 1, wherein $R_1$ is $OR_5$, wherein $R_5$ is H, an alkyl or acyl group having one to six carbon atoms.

8. The cyclic compound of claim 1, wherein the bond between $C_2$ and $C_3$ is a double bond.

9. The cyclic compound of claim 1, wherein the bond between $C_2$ and $C_3$ is a single bond.

10. A cyclic compound of the formula selected from the group consisting of -continued 11. A cyclic compound of formula wherein:
the bond between $C_2$ and $C_3$ is a single or a double bond;
$R_1$ is $OR_5$, wherein $R_5$ is H, an alkyl or acyl group having one to six carbon atoms or $CO_2R_6$ wherein $R_6$ is H or an alkyl group having one to six carbon atoms;
$R_2$ is an alkyl group having one to six carbon atoms;
each of $R_3$ and $R_4$ is independently an alkyl or alkenyl group having one to six carbon atoms, or a phenyl group which may be attached via an alkyl or alkenyl group having one to six carbon atoms or a halogen atom, or $R_3$ and $R_4$ may be taken together to form a methylidene, an alkylidene having one to six carbon atoms or an arylidene group; and
Y is H or an O-acyl substituted group.

12. The cyclic compound of claim 11, wherein $R_3$ and $R_4$ taken together form a group selected from:

13. The cyclic compound of claim 11, wherein each of $R_3$ and $R_4$ is independently an alkyl or alkenyl group having one to six carbon atoms, or a phenyl group which may be attached via an alkyl or alkenyl group having one to six carbon atoms or a halogen atom.

14. The cyclic compound of claim 11, wherein $R_2$ is a group selected from $CH_3$, $CH_2CH_3$, and i-pr.

15. The cyclic compound of claim 11, wherein $R_1$ is $CO_2R_6$ wherein $R_6$ is H or an alkyl group having one to six carbon atoms.

16. The cyclic compound of claim 11, wherein $R_1$ is $OR_5$, wherein $R_5$ is H, an alkyl or acyl group having one to six carbon atoms.

17. The cyclic compound of claim 11, wherein the bond between $C_2$ and $C_3$ is a double bond.

18. The cyclic compound of claim 11, wherein the bond between $C_2$ and $C_3$ is a single bond.

19. A cyclic compound of formula wherein: X is when specified in the $C_4$ to $C_n$ direction;
$R_1$ is $OR_5$, wherein $R_5$ is H, an alkyl or acyl group having one to six carbon atoms or $CO_2R_6$ wherein $R_6$ is H or an alkyl group having one to six carbon atoms;
$R_2$ is H, an alkyl or alkenyl group having one to six carbon atoms;
each of $R_3$ and $R_4$ is independently H, an alkyl or alkenyl group having one to six carbon atoms, or a phenyl group which may be attached via an alkyl or alkenyl group having one to six carbon atoms or a halogen atom, or $R_3$ and $R_4$ may be taken together to form a methylidene, an alkylidene having one to six carbon atoms or an arylidene group; and
Y is H, OH, or an O-acyl substituted group.

20. A composition useful as an anti-tumor promoter agent comprising a therapeutically effective amount of at least one cyclic compound of claim 1.

21. A composition useful as an anti-tumor promoter agent comprising a therapeutically effective amount of at least one cyclic compound of claim 11.

22. A composition useful as an anti-tumor promoter agent comprising a therapeutically effective amount of at least one cyclic compound of claim 19.

23. A method for preventing or treating tumors in a mammalian host, which comprises administering to said host a pharmaceutically effective amount of a cyclic compound according to claim 1.

24. A method for preventing or treating tumors in a mammalian host, which comprises administering to said host a pharmaceutically effective amount of a cyclic compound according to claim 11.

25. A method for preventing or treating tumors in a mammalian host, which comprises administering to said host a pharmaceutically effective amount of a cyclic compound according to claim 19.

* * * * *